(12) United States Patent
Sang et al.

(10) Patent No.: US 8,022,114 B2
(45) Date of Patent: Sep. 20, 2011

(54) DENTAL ADHESIVE COMPOSITIONS AND METHODS

(76) Inventors: Junjie Sang, Magnolia, DE (US); Huaibing Liu, Dover, DE (US); Xiuling Wang, Magnolia, DE (US)

( * ) Notice: Subject to any disclaimer, the term of this patent is extended or adjusted under 35 U.S.C. 154(b) by 13 days.

(21) Appl. No.: 12/653,251

(22) Filed: Dec. 10, 2009

(65) Prior Publication Data

US 2011/0112208 A1 May 12, 2011

Related U.S. Application Data

(63) Continuation of application No. 12/284,817, filed on Sep. 25, 2008, now abandoned, which is a continuation of application No. 11/899,124, filed on Sep. 4, 2007, now abandoned, which is a continuation of application No. 10/844,628, filed on May 13, 2004, now abandoned.

(60) Provisional application No. 60/469,938, filed on May 13, 2003.

(51) Int. Cl.
*A61K 6/083* (2006.01)
*C08F 2/50* (2006.01)

(52) U.S. Cl. .................. 523/118; 433/228.1; 522/47

(58) Field of Classification Search .................. 523/118; 433/228.1; 522/47
See application file for complete search history.

(56) References Cited

U.S. PATENT DOCUMENTS

| | | | |
|---|---|---|---|
| 4,372,836 A | 2/1983 | Schmitt et al. | |
| 4,389,497 A | 6/1983 | Schmitt et al. | |
| 4,503,169 A | 3/1985 | Randklev | |
| 4,544,359 A | 10/1985 | Waknine | |
| 4,602,076 A | 7/1986 | Ratcliffe et al. | |
| 4,636,533 A | 1/1987 | Janda et al. | |
| 4,640,936 A | 2/1987 | Janda et al. | |
| 4,674,980 A | 6/1987 | Ibsen et al. | |
| 4,696,955 A | 9/1987 | Kuhlmann | |
| 4,707,504 A | 11/1987 | Walkowiak et al. | |
| 4,721,735 A | 1/1988 | Bennett et al. | |
| 4,746,686 A | 5/1988 | Waller | |
| 4,767,798 A | 8/1988 | Gasser et al. | |
| 4,820,744 A | 4/1989 | Kubota et al. | |
| 4,906,446 A | 3/1990 | Engelbrecht et al. | |
| 4,959,297 A | 9/1990 | Palazzotto | |
| 4,966,934 A | 10/1990 | Huang et al. | |
| 5,004,501 A | 4/1991 | Faccioli et al. | |
| 5,033,650 A | 7/1991 | Colin et al. | |
| 5,091,441 A | 2/1992 | Omura | |
| 5,130,348 A | 7/1992 | Zahler et al. | |
| 5,264,513 A | 11/1993 | Ikemura et al. | |
| 5,321,053 A | 6/1994 | Hino et al. | |
| 5,376,691 A | 12/1994 | May et al. | |
| 5,530,038 A * | 6/1996 | Yamamoto et al. | ........... 523/116 |
| 5,554,665 A | 9/1996 | Tateosian et al. | |
| 5,658,963 A | 8/1997 | Qian et al. | |
| 5,739,177 A | 4/1998 | Ohno et al. | |
| 5,866,631 A | 2/1999 | Nakagawa et al. | |
| 5,932,627 A | 8/1999 | Blackwell | |
| 6,071,983 A | 6/2000 | Yamamoto et al. | |
| 6,114,408 A | 9/2000 | Dickens | |
| 6,147,137 A | 11/2000 | Jia | |
| 6,174,935 B1 | 1/2001 | Matsunae et al. | |
| 6,191,190 B1 | 2/2001 | Blackwell et al. | |
| 6,245,872 B1 | 6/2001 | Frey et al. | |
| 6,288,138 B1 * | 9/2001 | Yamamoto et al. | ........... 523/118 |
| 6,372,816 B1 | 4/2002 | Walz et al. | |
| 6,387,979 B1 | 5/2002 | Hino | |
| 6,387,980 B2 | 5/2002 | Lu et al. | |
| 6,387,982 B1 | 5/2002 | Blackwell | |
| 6,458,869 B1 | 10/2002 | Antonucci et al. | |
| 6,482,871 B1 | 11/2002 | Aasen et al. | |
| 6,592,372 B2 | 7/2003 | Jia et al. | |
| 6,649,669 B2 | 11/2003 | Dickens | |
| 6,660,784 B2 | 12/2003 | Ibaragi et al. | |
| 6,759,449 B2 | 7/2004 | Kimura et al. | |
| 6,815,470 B2 | 11/2004 | Ibaragi et al. | |
| 7,166,651 B2 | 1/2007 | Qian | |
| 7,226,960 B2 * | 6/2007 | Jia | ................. 523/115 |
| 2003/0055124 A1 | 3/2003 | Klee et al. | |
| 2003/0092788 A1 | 5/2003 | Galstian et al. | |
| 2003/0171450 A1 | 9/2003 | Wang et al. | |
| 2003/0186196 A1 | 10/2003 | Wang et al. | |
| 2003/0187092 A1 | 10/2003 | Fujiwara | |
| 2003/0207960 A1 | 11/2003 | Jia | |
| 2004/0006154 A1 | 1/2004 | Ibaragi et al. | |
| 2005/0009946 A1 | 1/2005 | Oguri et al. | |

FOREIGN PATENT DOCUMENTS

| | | | |
|---|---|---|---|
| EP | 0363903 A2 | 4/1990 | |
| EP | 0948956 A2 | 10/1999 | |
| EP | 1051961 A1 | 11/2000 | |
| EP | 1346717 A1 | 9/2003 | |
| EP | 1402872 A1 | 3/2004 | |
| EP | 1479364 A1 | 11/2004 | |
| EP | 1502569 A1 | 2/2005 | |
| WO | 03013444 A1 | 2/2003 | |
| WO | 2004100900 A1 | 11/2004 | |
| WO | 2006044223 A1 | 4/2006 | |

\* cited by examiner

*Primary Examiner* — Tae H Yoon

(74) *Attorney, Agent, or Firm* — Douglas Hura; Leana Levin; David Zdurne

(57) ABSTRACT

Two-part and one-part self-etching dental adhesives containing polymerizable acidic monomers. Methods include one-coat application without need for tooth etching.

6 Claims, No Drawings

DENTAL ADHESIVE COMPOSITIONS AND METHODS

RELATED APPLICATION

This application is a continuation of U.S. patent application Ser. No. 12/284,817 having a filing date of Sep. 25, 2008 now abandoned which is a continuation of U.S. patent application Ser. No. 11/899,124 having a filing date of Sep. 4, 2007 now abandoned which is a continuation of U.S. patent application Ser. No. 10/844,628 having a filing date of May 13, 2004 now abandoned which claims the benefit of Provisional Application No. 60/469,938 filed on May 13, 2003.

TECHNICAL FIELD

The present invention generally relates to dental adhesives. More particularly the invention relates to self-etching adhesives. Specifically the invention relates to adhesives containing polymerizable acidic monomers.

BACKGROUND OF THE INVENTION

Table of Abbreviations Used Herein

| Abbreviation | Full term |
|---|---|
| 4-META | 4-methacryloxyethyltrimellitic Anhydride |
| AHPMA | 3-(Acryloyloxy)2-hydroxypropyl methacrylate |
| BHT | Butylated Hydroxytoluene |
| BMAP | Bis(2-methacryloxyethyl) phosphate |
| CAF | Cetylamine Hydrofluoride |
| CQ | Camphorquinone |
| DHEPT | Dihydroxylethyl-p-toluidine |
| DMABA | Dimethylaminobenzoic acid |
| DMABN | Dimethylaminobenzonitrile |
| EDAB | 4-ethyldimethylaminbenzoate |
| EGMP | Ethylene glycol methacrylate phosphate |
| HEMA | 2-Hydroxyethyl methacrylate |
| L-TPO | Diphenyl (2,4,6-trimethylbenzoyl) phosphine oxide |
| NaTs | Sodium salt of p-toluenesulfinic acid |
| OEMA | 4,4'-Oxydiphenylether 1,1',6,6'-tetracarboxylic acid-1,1'-(2-methacryloxy) dimethacrylate |
| PENTA | Dipentaerythritol pentaacrylate phosphoric acid ester |
| PyroEMA | Tetra-methacryloxyethyl Pyrophosphate |
| SBS | Shear Bond Strength |
| SCA | Self-cure activator |
| SEA | Self-etching adhesive |
| 2P-SEA | Two-Part Self-etching adhesive |
| 1P-SEA | One-Part Self-etching adhesive |
| VLC | Visible Light Cure |
| SC | Self Cure (or antocure) |
| SUM | summation |
| TEGDMA | Triethyleneglycoldimethacrylate |
| TMPTMA | Trimethylolpropane Trimethacrylate |
| UDMA | 1,6-Bis[methacryloyloxyethoxycarbonylamino]-2,4,4-tromethylhexane |

As used herein all "%" and percents or the like are by weight.

With the use of composite resins as dental restorative materials, it is required to ensure firm adhesion between tooth structures and composite resins by a simple handling. A representative adhesive restoration procedure includes an acid etching on tooth substrate by phosphoric acid, followed by water rinsing, drying, application of a primer, drying, application of a bonding agent, light-curing and finally filling of a composite resin. It is apparent that it takes time in many bonding steps to accomplish such handling and that no adhesion with confidence is attained.

In order to reduce the number of constituents to be used, priming and bonding were combined in one-bottle, so-called one-bottle/two-step, exemplified by Prime & Bond® brand adhesive (Dentsply). Etching must still be carried out first, followed by the application of the single-bottle bonding at least once and then polymerization, before the filling materials is used. Another simplification of the process for the adhesive securing of filling materials is to combine priming and etching into one-component, so-called self-etching primers, such as SE Primer in ClearFil SE Bond system [a 2-component (SE Primer and Bond liquid), 2-step, sequentially applied (SE Primer, followed by Bond resin) self-etching adhesive by Kuraray]. ClearFil SE Bond is indicated for direct light cured composite restoration bonding only. For indirect restoration bonding, Kuraray recommends using ClearFil Liner Bond 2V that is a multi-component (Primers A and B, Bond Liquid A and B)/multi-steps application self etching adhesive system.

Adper Prompt L-Pop (3M ESPE), so-called 2-component/one-pack/one-step self-etching and self-priming adhesive, is supplied in a Single Unit Dose blister package that consists of two-predosed compartments, or in two separate bottles for the two liquids A and B. Prompt L-Pop is indicated for direct light cured composite restoration bonding only.

Ref. U.S. Pat. No. 6,387,979 by K. Hino (Kuraray Co. Ltd., Japan), issued May 14, 2002 describes a tooth treated with a bonding composition with high initial bonding strength and good bonding durability comprising a mixture of polymerizable compound having an acid group, a water-soluble film-forming agent, water, and a curing agent, in which the calcium salt of the acid is insoluble in water, and the film-forming agent is a polymerizable compound miscible with a physiological saline solution, does not require any pre-treatment such as acid-etching or priming treatment. It is stated that the active ingredients of the composition in a single package may degrade or polymerize while stored. To prevent this, the constituent ingredients of the composition may be divided into two or more parts. The plural parts are separately packaged and stored in different packages. For their use, the plural parts taken out of the individual packages may be applied to one and the same object in sequence; or they may be blended into one mixture just before use.

PREFERRED EMBODIMENTS FOR CARRYING OUT THE INVENTION

In a preferred embodiment of the present invention, a dental adhesive comprises:
(i) from about 5 to about 70% by weight of polymerizable acids components selected from the group consisting of PENTA, OEMA and mixtures thereof;
(ii) from about 1 to about 30% by weight of hydrophilic methacrylate;
(iii) from about 1 to about 25% by weight of hydrophilic difunctional (meth)acrylate;
(iv) from about 1 to about 35% by weight of Urethane methacrylate;
(v) from about 1 to about 30% by weight of hydrophobic difunctional (meth)acrylate;
(vi) from about 0.1 to about 5% photoinitiator of (phosphine oxide, and/or CQ/co-initiator selected from the group consisting of Lucerin TPO, CQ/EDAB and CQ/DMABN);
(vii) from about 0.1 to about 5% curing additives selected from the group consisting of aromatic sulfinate salts;

(viii) from about 0.1 to about 5% fluoride-releasing ingredient selected from the group consisting of cetylamine hydrofluoride (CAF);
(ix) from about 0.1 to about 10% filler particles selected from the group consisting of fumed silica and functionalized nano-particles;
(x) from about 0.05 to about 2% stabilize;
(xi) from about 1 to about 40% water; and
(xii) from about 5 to about 60% water-miscible polar organic solvent selected from the group consisting of acetone and alcohol.

In another preferred embodiment, a dental adhesive comprises:
(i) from about 5 to about 50% by weight of polymerizable acids components selected from the group consisting of PENTA, 4-META and mixtures thereof;
(ii) from about 1 to about 20% by weight of hydrophilic methacrylate;
(iii) from about 1 to about 15% by weight of hydrophilic difunctional (meth)acrylate;
(iv) from about 1 to about 30% by weight of Urethane dimethacrylate;
(v) from about 1 to about 30% by weight of hydrophobic difunctional (meth)acrylate;
(vi) from about 0.1 to about 5% photoinitiators of (phosphine oxide, and/or CQ/co-initiator selected from the group consisting of Lucerin TPO, CQ/DMABN combination and L-TPO/CQ/EDAB combination);
(vii) from about 0.1 to about 5% curing additives selected from the group consisting of aromatic sulfinate salts;
(viii) from about 0.1 to about 5% fluoride-releasing ingredient selected from the group consisting of cetylamine hydrofluoride (CAF);
(ix) from about 0.1 to about 10% filler particles selected from the group consisting of fumed silica and functionalized nano-particles;
(x) from about 0.05 to about 2% stabilize;
(xi) from about 1 to about 35% water; and
(xii) from about 5 to about 60% water-miscible polar organic solvent selected from the group consisting of acetone or alcohol.

According to the present invention, there is provided both Two-component and One-component Self-Etching Adhesive (2P-SEA, and 1P-SEA). The new self-etching adhesive materials achieve good adhesion performance with a simple one-coat application, without the need of tooth etching using phosphoric acid tooth gel in its specific indications.

2P-SEA is a LC/SC Dual Cure Self-Etching Adhesive system that is applied onto tooth cavity surfaces with premixed Solutions A and B prior to bonding the direct light cure composite restorations or indirect cemented restorations. The preferred 2P-SEA composition contains optimized mixture of polymerizable acidic monomers with phosphoric acid and/or carboxylic acid groups, various hydrophilic and hydrophobic meth(acrylates) monomers, structure resin monomer, crosslinker, curing agent (L-TPO plus CQ/EDAB (or CQ/DMABN) and cure-promoting additives (NaTs), stabilizer, water and other solvents (such as Acetone, or other alcohols (methanol, ethanol, t-butanol)). Unlike previous self-etching adhesives, the 2P-SEA solution according to the invention can be used to bond both Visible Light Cured (VLC) composite type restorations and cemented indirect restorations (prefabricated metal/porcelain/composite Inlays/Onlays/Veneers/Crowns/Bridges) to human teeth substrate (enamel and dentine) without the need of separate acid-etching or priming pre-treatment teeth bonding step. The 2P-SEA application procedure remains the same, i.e. [Part A/B Mix ratio=2/1 by w/w/ or v/v, 1Coat/20 seconds wet, air dry, LC 10" or 20"], whether it is for direct or indirect bonding restorations. The 2P-SEA also showed improved bonding performance over prior art products, with enamel bond strength of at least greater than 20 MPa and dentin bond strength of at least greater than 15-20 MPa. The bonding performance sustained even after excessive thermal stressing (1800×, or 5000×, 55/5-° C. thermal cycling) or up to 12 week/50° C. thermal aging, indicating good bonding durability and materials shelf-life stability. In comparison with current commercial Self-Etching Adhesive products, 2P-SEA also shows better or equivalent bonding performance, with more versatility in applications.

1P-SEA according to the inventions is a Single Step Light Cured Self-Etching Adhesive that is contained in one single package (bottle or single unit-dose) prior to applying onto tooth cavity surfaces to bond the direct light cure composite type restorations. The preferred 1P-SEA composition contains optimized mixture of polymerizable acidic monomers with phosphoric acid and/or carboxylic acid groups, various hydrophilic and hydrophobic meth(acrylates) monomers, structure resin monomer, crosslinker, curing agent (L-TPO and/or CQ/DMABN (or CQ/EDAB), stabilizer, water and other solvents (acetone, or alcohol). Unlike previous self-etching adhesives, one-component SEA materials shows high initial bonding strength and good bonding durability and long-term bonding performance as well, with enamel bond strength of at least greater than 20 MPa and dentin bond strength of at least greater than 15-20 MPa. The new 1P-SEA materials achieve good adhesion performance with a simple "one-coat" application technique, without separate acid-etching or tooth-priming step. The bonding performance of 1P-SEA sustains even after excessive thermal stressing (1800× or 5000×, 55/5-° C. thermal cycling) or 4 week/50° C. thermal aging, indicating good bonding durability and materials shelf-life stability. In comparison with current commercial Self-Etching Adhesive products, 1P-SEA shows better or equivalent bonding performance, with better storage stability and longer shelf life. The 1P-SEA shows improved bonding performance over prior art products, with high initial and sustained long-term bonding performance [enamel bond strength of at least greater than 20 MPa and dentin bond strength of at least greater than 15-20 MPa] and good bonding durability. Unlike prior art self-etching adhesive products in which the active ingredients of the composition have to be divided into two or more parts in different packages to avoid composition degradation or polymerization, the 1P-SEA overcome the one-package storage stability issue by choosing the optimum ingredients of appropriate acidic strength acidic monomers, effective and stable VLC photoinitiator in acidic aqueous solution, A bifunctional hydrophilic monomer with higher crosslinking and less tendency to hydrolysis, and minimum amount of water incorporated into a water-miscible polar aprotic organic solvent. Optionally, micro- or nanosized fillers and fluoride-releasing agent can also be added to enhance the product performance and provide fluoride release feature. When used with a separate Self-Cure Activator component, the 1P-SEA application can be expanded to bond cemented indirect restorations (prefabricated metal/porcelain/composite Inlays/Onlays/Veneers/Crowns/Bridges) with human teeth substrate (enamel and dentine) without separate acid-etching or priming pre-treatment step.

Both 2P-SEA, and 1P-SEA materials can achieve good adhesion performance with a simple one-coat application, without the need of using phosphoric acid tooth gel in its specific indications as follows.

For Two-component Dual Cure Self-Etching Adhesive (2P-SEA), it is indicated to bond both Visible Light Cure (VLC) composite/compomer direct restorations and cemented indirect restorations (prefabricated metal/porcelain/composite Inlays/Onlays/Veneers/Crowns/Bridges) to human teeth substrate (enamel and dentine) without the need of separate acid-etching or priming pre-treatment teeth bonding step. Whether it is used for direct or indirect bonding restorations, the 2P-SEA application procedure remains the same, i.e. [Part A/B Mix ratio=2/1 by w/w/ or v/v, 1Coat/20 seconds wet, air dry, LC 10 or 20 seconds]. In addition, the 2P-SEA can also be used for adhesive repairs of tooth restorations (composite/porcelain/amalgam). It can also be used as a cavity varnish or desensitizer.

For One-component Visible Light Cure Self-Etching Adhesive (1P-SEA), it is indicated to bond VLC composite/compomer direct restorations to human teeth substrate (enamel and dentine) without the need of separate acid-etching or priming pre-treatment teeth bonding step. When used with a separate Self-Cure Activator component, the 1P-SEA can also bond for cemented indirect restorations (prefabricated metal/porcelain/composite Inlays/Onlays/Veneers/Crowns/Bridges) to human teeth substrate (enamel and dentine) without separate acid-etching or priming pre-treatment step. In addition, 1P-SEA can also be used as a cavity varnish or desensitizer.

Both Two-component and One-component Self-Etching Adhesive (2P-SEA, and 1P-SEA) prototypes developed represent an improvement to the existing commercial self-etching adhesive products. The new self-etching adhesive materials achieve good adhesion performance with a simple one-coat application, without the need of separate acid-etching or priming pre-treatment teeth bonding step.

The property improvement results from the unique composition of 2P-SEA which comprises of an optimized mixture of acidic adhesion promoters with phosphoric acid and/or carboxylic acid functional groups (e.g. PENTA and OEMA), various hydrophilic and hydrophobic meth(acrylates) monomers, curing agent (L-TPO plus CQ/EDAB (or CQ/DMABN or other photo-coinitiator) and cure-promoting additives sulfinate salts, NaTs), water and volatile polar solvents (acetone, or alcohol). Unlike previous commercialized multi-component self-etching adhesives, the 2P-SEA Dual Cure can be used to bond both direct VLC composite type restorations and cemented indirect restorations (prefabricated metal/porcelain/composite Inlays/Onlays/Veneers/Crowns/Bridges) to human teeth substrate (enamel and dentine) without the need of separate acid-etching or priming pre-treatment teeth bonding step. The application procedure of 2P-SEA remains the same, i.e. [Part A/B Mix ratio=2/1 by w/w/ or v/v, 1Coat/20 seconds wet, air dry, LC], whether it is for direct or indirect bonding restorations. The 2P-SEA also showed improved bonding performance over prior art products, with enamel bond strength of at least greater than 20 MPa and dentin bond strength of at least greater than 18 (15-20) MPa. The bonding performance sustained even after excessive thermal stressing (1800× or 5000×, 55/5-° C. thermal cycling) or up to 12 week/50° C. thermal aging, indicating good bonding durability and materials shelf-life stability. In comparison with current commercial Self-Etching Adhesive products, 2P-SEA also shows better or equivalent bonding performance, with more versatility in applications (see attached Comparison to Competitions).

A first Two-component LC/SC Dual Cure SEA has the following characteristics:
  Bond both direct and indirect with same simple application technique;
  Simple system (2 bottle or single unit dose packaged, no rinse/no "dry & wet issues, no more sensitivity);
  Easy to use (one coat/1-step application technique);
  High Bonding Performance and Durable (stable);
  Versatility (2 bottle adhesive system for both direct and Indirect restoration bonding applications); and,
  2+ year shelf life (no refrigeration needed).

1P-SEA is a Light Cured Self-Etching Adhesive contained in one single package (bottle or single unit-dose) prior to applying onto tooth cavity surfaces to bond the direct light cure composite type restorations. Unlike prior art self-etching adhesive products of which the active ingredients of the composition have to be divided into two or more parts in different packages to avoid composition degradation or polymerization, the 1P-SEA overcome the one-package storage stability issue by choosing the optimum ingredients required for good self-etching adhesion performance without presenting the hydrolysis stability issues commonly seen in other self-etching adhesives. The improved adhesion property and feature/benefits offered by 1P-SEA are made possible by optimum combination of 1P-SEA compositions, preferably comprised of appropriate acidic strength adhesion monomers (PENTA, 4-META, and other acidic monomers), effective and stable VLC photoinitiator in the acidic aqueous solution, a bifunctional hydrophilic monomer with higher crosslinking and less tendency to hydrolysis, and minimum amount of water incorporated into a water-miscible polar aprotic organic solvent. Optionally, micro- or nanosized fillers and fluoride-releasing agent can also be added to 1P-SEA composition to enhance the product performance and provide fluoride release feature. When used with a separate Self-Cure Activator component, the 1P-SEA application can be expanded to bond cemented indirect restorations (prefabricated metal/porcelain/composite Inlays/Onlays/Veneers/Crowns/Bridges) with human teeth substrate (enamel and dentine) without separate acid-etching or priming pre-treatment step. The 1P-SEA shows improved bonding performance over prior art products, with high initial and sustained long-term bonding performance [enamel bond strength of at least greater than 20 MPa and dentin bond strength of at least greater than 15-20 MPa] and good bonding durability. The new 1P-SEA materials achieve good adhesion performance with a simple "one-coat" one-step application technique, without separate acid-etching or tooth-priming step. The bonding performance of 1P-SEA sustains even after excessive thermal stressing (5000×, 55/5-° C. thermal cycling) or 4 week/50° C. thermal aging, indicating good bonding durability and materials shelf-life stability. In comparison with current commercial Self-Etching Adhesive products, 1P-SEA shows better or equivalent bonding performance, with better storage stability and longer shelf life (see attached Comparison to Competitions).

A TRUE one-component SEA has the following characteristics:
  Simple (1 bottle or single unit dose packaged, no mix/no rinse/no "dry & wet issues, no more sensitivity);
  Fast and Easy (one coat/1-step within 40");
  High Bonding Performance and Durable (stable);
  2 year shelf life;
  Fluoride releasing; and,
  Versatility (expandable to Indirect Applications with Self Cure Activator component).

General Experimental

The compositions according to the present invention variously contain the following components which are listed with their appropriate functions.
  PENTA: Acidic monomer, adhesion promoter;
  OEMA: Acidic monomer, adhesion promoter;

(4-META: Acidic monomer, adhesion promoter);
AHPMA: Difunctional hydrophilic monomer, wetting agent;
HEMA: Monofunctional hydrophilic monomer, wetting agent;
TEGMA: Reactive diluent;
UDMA: Structural resin;
TMPTMA: Crosslinker;
Photoinitiators and stabilizers;
Curing additives: sulfinate salts NaTs;
Acetone (or alcohol): Solvent, resin carrier; and,
Water: ionizing medium for protonic acid, solubilizing medium for calcium salts, essential for effective enamel etching.

It is desired to have the following characteristics:
Minimum amount of water incorporated;
Water miscible polar aprotic organic solvent, eg. acetone as solvent to minimize hydrolysis and solvolysis;
L-TPO as VLC photoinitiator: effective and stable in acidic aqueous solution. L-TPO plus CQ/DMABN or CQ/EDAB can be cured effectively by both typical dental halogen QTH or LED curing units;
for 1P-SEA, a bifunctional hydrophilic monomer included: higher crosslinking, less prone to hydrolysis and less contributing to a medium favorable for hydrolysis; and,
for 1P-SEA, appropriate acidic strength of acidic monomers were identified, that are strong enough to etch both dentin and enamel, but with adequate hydrolytic stability.

Several series of LC/SC Dual Cure Two-part SEA with good bonding performance were identified, with the preferred 2P-SEA composition and formulations (LCH57-78-2/LCH56-140) listed in the attachment. the 2P-SEA Dual Cure can be used to bond both direct VLC composite type restorations AND cemented indirect restorations to human teeth substrate (enamel and dentine) without the need of separate acid-etching or priming pre-treatment teeth bonding step.

The 2P-SEA also showed improved bonding performance over prior art products, with enamel bond strength of at least greater than 20 MPa and dentin bond strength of at least greater than 18 (15-20) MPa. The bonding performance sustained even after excessive thermal stressing (1800× or 5000×, 55/5-° C. thermal cycling) or up to 12 week/50° C. thermal aging, indicating good bonding durability and materials shelf-life stability.

Two very promising one-part SEA inventions were identified. One embodiment of the 1P-SEA invention contains PENTA as acidic monomer and another has PENTA/4-META as acidic monomers.

L-TPO as VLC photoinitiator: effective and stable in acidic aqueous solution. L-TPO plus CQ/DMABN or CQ/EDAB photoinitiator combination is stable in acid environment, and can be cured effectively by both typical dental halogen QTH or LED curing units.

They exhibited excellent baseline bond strength on both dentin and enamel. On storage 50° C./3 weeks, they still had acceptable bond strength to both dentin and enamel (dentin SBS greater than 15 MPa and enamel SBS greater than 20 MPa).

The BS samples applied with the new SEA invention were thermocycled 55-5° C. for 1800 cycles or 5000×. No significant change in both dentin and enamel bond strength was observed.

Samples Preparation and Testing for Measuring Shear Bond Strength of Composite Restoratives or Cemented Indirect Restorations (Inlays/Onlays/Crowns/Bridges) to Human Tooth Substrates (Dentin or Enamel) Using SEA (2P-SEA or 1P-SEA)

The extracted human molars were immersed in water and stored in a 4° C. refrigerator prior to use. Dentin or enamel was sanded using wet 320 grit abrasive paper and then 600 grit. A dental adhesive was applied to dentin or enamel surface and scrubbed with a microbrush for 20 seconds. The surface was blown dry 10 seconds with air stream and light cured 10 seconds using Spectrum 800 at 550 mw/cm$^2$. Gelatin capsules (#5) were half-filled with TPH composite and cured in a VL curing oven. The capsules were filled with TPH and positioned onto the coated dentin. The flash was gently removed using a dental explorer and the composite was light cured 3×20" sequentially around the circumference of the cylinder with Spectrum 800 at 550 mw/cm$^2$.

For indirect cementation bond strength, The capsules or plastic matrix were filled with mixed composite resin cements (e.g. Calibra resin cement by Dentsply) and positioned onto the coated dentin or enamel surface. The flash was gently removed using a dental explorer and the restorative post was light cured 3×20" sequentially around the circumference of the cylinder with Spectrum 800 at 550 mw/cm$^2$, or leaves self-cure for resin cement.

The samples were embedded in tray resin and the posts were ensured to be perpendicular to the bonding surface. The shear bond strength was obtained in compressive shear mode with a Instron at a crosshead speed of 5 mm/min). The similar procedure was followed to test enamel shear bond strength except that plastic straws with smaller diameter were used instead of gelatin capsules.

EXAMPLES

2P-SEA Example 1

A 2P-SEA comprises of liquid A and Liquid B. The liquid A is comprised of 20.0 parts by weight of dipentaerythritol pentaacrylate phosphoric acid ester (PENTA), 15.0 parts by weight of OEMA resin, 5 parts by weight of hydroxyethyl methacrylate (HEMA), 10.0 parts by weight of triethyleneglycoldimethacrylate (TEGDMA), 5.0 parts by weight of 1,6-Bis (methacryloyloxyethoxycarbonylamino)-2,4,4-trimethylhexane (UDMA), 2.0 parts by weight of trimethylolpropane trimethacrylate (TMPTMA), 2.0 parts by weight of diphenyl (2,4,6-trimethylbenzoyl) phosphine oxide (L-TPO), 0.30 parts by weight of camphouquinone (CQ), and 1.0 parts of EDAB (or 1.0 parts of the 4-dimethylaminobenzonitrile (DMABN), 0.40 part by weight of butylated hydroxytoluene (BHT), 44.3 parts by weight of solvent acetone (or ethanol, or 2-methyl-2-propanol, or methanol,). The liquid B is comprised of 2.0 parts by weight of sodium aromatic sulfinate (NaTs), 19.9 parts by weight of ethanol, and 78.1 parts by weight of deionized water. The 24 hour composite to dentin and enamel bond strength was measured 17.9(1.6) MPa and 30.0(5.6) MPa, respectively, without separate etching step. The 24 hour composite resin cement (Calibra) to dentin and enamel bond strength was measured as 19.6(5.8) MPa and 23.3(6.6) MPa, respectively, without separate etching step. The thermal cycled (1800 cycle, between 55/5° C.) composite to dentin and enamel bond strength was measured 16.5 (2.8) MPa and 35.6 (3.3) MPa, respectively, without separate etching step.

2P-SEA Example 2

LCH68-119-2&LCH68-120-2

A 2P-SEA comprises of Liquid A and Liquid B. The Liquid A is comprised of 35.0 parts by weight of dipentaerythritol pentaacrylate phosphoric acid ester (PENTA), 10.0 parts by weight of OEMA resin, 10.0 parts by weight of triethyleneglycoldimethacrylate (TEGDMA), 10.0 parts by weight of 1,6-Bis (methacryloyloxyethoxycarbonylamino)-2,4,4-trimethylhexane (UDMA), 2.0 parts by weight of trimethylolpropane trimethacrylate (TMPTMA), 2.0 parts by weight of diphenyl (2,4,6-trimethylbenzoyl) phosphine oxide (L-TPO), 0.30 parts by weight of camphouquinone (CQ), and 1.0 parts of EDAB, 0.40 part by weight of butylated hydroxytoluene (BHT), 29.3 parts by weight of 2-methyl-2-propanol. The liquid B is comprised of 2.0 parts by weight of sodium aromatic sulfinate (NaTs), 49.9 parts by weight of ethanol, and 48.1 parts by weight of deionized water. The 24 hour composite to dentin and enamel bond strength was measured as 19.5(1.3) MPa and 25.3(4.7) MPa, respectively, without separate etching step. The 24 hour composite resin cement (Calibra) to dentin and enamel bond strength was measured as 15.5(1.7) MPa and 27.2(2.0) MPa, respectively, without separate etching step.

Direct and Indirect Adhesion of Long-Term (18 Months) Room Temperature Aged 2P-SEA Materials The adhesion SBS study for 1.5 year (18 months) room ambient temperature aged above 2P-SEA Dual Cure adhesive materials (Lot#33801 & Lot#33201) showed direct composite enamel SBS of 27.0 MPa (100% cohesive failure) and dentin SBS of 18.0 MPa (100% cohesive failure), while a Indirect cementation enamel SBS of 24.5 MPa (100% cohesive failure) and dentin SBS of 14.4 MPa (60% cohesive failure) were also obtained for the same 2P-SEA materials using the same technique for both direct and indirect applications. Those results demonstrated that the 2P-SEA material has very good stability and adhesion results, with at least 1.5-year (18 months) shelf life at room temperature so far.

2P-SEA Example 3

A 2P-SEA comprises of Liquid A and Liquid B. The Liquid A is comprised of 20.0 parts by weight of dipentaerythritol pentaacrylate phosphoric acid ester (PENTA), 15.0 parts by weight of OEMA resin, 10.0 parts by weight of triethyleneglycoldimethacrylate (TEGDMA), 5.0 parts by weight of 1,6-Bis (methacryloyloxyethoxycarbonylamino)-2,4,4-trimethylhexane (UDMA), 2.0 parts by weight of trimethylolpropane trimethacrylate (TMPTMA), 2.0 parts by weight of diphenyl (2,4,6-trimethylbenzoyl) phosphine oxide (L-TPO), 0.30 parts by weight of camphouquinone (CQ), and 1.0 parts of EDAB, 0.40 part by weight of butylated hydroxytoluene (BHT), 0.2% cetylamine hydrofluoride (CAF) and 1% silanated fumed silica (Aerosil 380), 42.0 parts by weight of 2-methyl-2-propanol (or ethanol or Acetone). The liquid B is comprised of 2.0 parts by weight of sodium aromatic sulfinate (NaTs), 19.9 parts by weight of ethanol, and 78.1 parts by weight of deionized water. The 24 hour composite to dentin and enamel bond strength was measured as 21.8(2.2)) MPa and 25.0(3.1) MPa, respectively, without separate etching step. The 24 hour composite resin cement (Calibra) to dentin and enamel bond strength was measured as 13.1(2.5) MPa and 22.6(3.9) MPa, respectively, without separate etching step.

2P-SEA Example 4

Aqueous SCA LCH68-120-2

An aqueous Self Cure Activator (SCA) as 2P-SEA Liquid B was prepared according to the following procedures. The liquid B is comprised of 2.0 parts by weight of sodium aromatic sulfinate (NaTs), 49.9 parts by weight of ethanol, and 48.1 parts by weight of deionized water. The above 2P-SEA Liquid B can be used with any 2P-SEA Liquid A as described or used with other one-component dental adhesives in the intended direct composite or indirect cementation bonding applications.

1P-SEA Example 1

A mixture comprising 3.3 parts by weight of 4-methacryloxyethyltrimellitic anhydride (4-META), 13.3 parts by weight of dipentaerythritol pentaacrylate phosphoric acid ester (PENTA), 6.7 parts by weight of 3-(acryloyloxy)-2-hydroxypropyl methacrylate (AHPMA), 3.3 parts by weight of triethyleneglycoldimethacrylate (TEGMA), 10.9 parts by weight of 1,6-Bis(methacryloyloxyethoxycarbonylamino)-2,4,4-trimethylhexane (UDMA), 1.7 parts by weight of trimethylolpropane trimethacrylate (TMPTMA), 1.7 parts by weight of diphenyl (2,4,6-trimethylbenzoyl) phosphine oxide, 0.13 part by weight of butylated hydroxytoluene, 42.3 parts by weight of acetone and 16.7 parts by weight of deionized water were prepared. The dentin and enamel bond strength was measured 22.4 MPa and 33.8 MPa, respectively. The thermal cycled (1800 cycle, between 55/5° C.) composite to dentin and enamel bond strength was measured 25.5 MPa and 25.9 MPa, respectively, without separate etching step. The more excessive 5000× thermal cycled composite to dentin and enamel bond strength was measured as 25.0 MPa and 28.3 MPa, respectively, without separate etching step. The sustained thermal cycled enamel and dentin bond strength indicated the good bond durability and potential good long-term bonding performance in a clinical setting.

1P-SEA Example 2

A mixture comprising 25.0 parts by weight of dipentaerythritol pentaacrylate phosphoric acid ester (PENTA), 7.9 parts by weight of 3-(acryloyloxy)-2-hydroxypropyl methacrylate (AHPMA), 5.5 parts by weight of 2-hydroxyethyl methacrylate (HEMA), 10.9 parts by weight of 1,6-Bis (methacryloyloxyethoxycarbonylamino)-2,4,4-trimethylhexane (UDMA), 1.7 parts by weight of trimethylolpropane trimethacrylate (TMPTMA), 1.7 parts by weight of diphenyl (2,4,6-trimethylbenzoyl) phosphine oxide, 0.13 part by weight of butylated hydroxytoluene, 42.3 parts by weight of acetone and 16.7 parts by weight of deionized water were prepared. The dentin and enamel bond strength was measured 21.4 MPa and 26.3 MPa, respectively. The thermal cycled (1800 cycle, between 55/5° C.) composite to dentin and enamel bond strength was measured 21.1 MPa and 28.3 MPa, respectively, without separate etching step.

1P-SEA Example 3

50° C. Accelerated Storage Stability Test of Two Representative Formulations

TABLE 1

SEA formulations and bond strength

| Formulation Component | HL2-5 % wt | HL2-7 % wt |
|---|---|---|
| PENTA | 25.0 | 20.0 |
| 4-META | 0 | 3.3 |
| AHPMA | 7.9 | 0 |

TABLE 1-continued

SEA formulations and bond strength

| Formulation Component | HL2-5 % wt | HL2-7 % wt |
|---|---|---|
| HEMA | 0 | 3.3 |
| UDMA | 3.5 | 9.9 |
| TMPTMA | 1.7 | 1.7 |
| L-TPO | 1.7 | 1.7 | shear bond strength of HL1-72-4 and HL1-72-5 was 5.7(1.3) MPa and 2.3 (2.4) MPa, respectively; the enamel shear bond strength of HL1-72-4 was 2.2 (1.0) while posts fell off during storage for HL1-72-5 enamel SBS test. Even when enamel was etched with Caulk 34% Tooth Conditioner Gel, the bond strength of HL1-72-4 stored at 50° C. for three weeks was only 4.8(0.7) MPa. This suggests that a disastrous hydrolysis of resins in the formulation has occurred and the reduced mechanical strength of cured resins leads to the lowered bond strength.

TABLE 2

50° C. Accelerated Storage Stability Test on PENTA/BMAP based one-component aqueous formulations

| Sample I.D. | Shear Bond Strength (MPa) | 0 week 50° C. | 1 week 50° C. | 2 week 50° C. | 3 week 50° C. |
|---|---|---|---|---|---|
| HL1-72-4 | Dentin | 10.9 (4.7) | 9.7 (2.9) | 5.6 (3.5) | 5.7 (1.3) |
| | Enamel | 33.4 (2.0) | | | 2.2 (1.0) |
| HL1-72-5 | Dentin | 10.9 (6.3) | | | 2.3 (2.4) |
| | Enamel | 27.4 (4.7) | | | Posts fell off |

TABLE 1-continued

SEA formulations and bond strength

| Formulation Component | | HL2-5 % wt | HL2-7 % wt |
|---|---|---|---|
| BHT | | 0.13 | 0.13 |
| Acetone | | 41.7 | 43.3 |
| Water | | 18.3 | 16.7 |
| SUM | | 100 | 100 |
| Dentin SBS (MPa): mean(SD) | 0 week 50° C. | 21.4 (3.9) | 22.4 (5.2) |
| | 2 week 50° C. | 17.8 (5.8) | 14.2 (4.2) |
| | 3 week 50° C. | 17.6 (6.4) | 21.8 (0.7) |
| | 4 week 50° C. | 8.2 (2.2) | 14.8 (2.1) |
| Enamel SBS (MPa): mean(SD) | 0 week 50° C. | 26.3 (4.6) | 33.8 (3.1) |
| | 2 week 50° C. | 30.6 (11.1) | 19.7 (3.1) |
| | 3 week 50° C. | 29.4 (12.0) | 24.2 (9.0) |
| | 4 week 50° C. | 14.4 (4.1) | 12.8 (7.8) |

1P-SEA Example 4

50° C. Accelerated Storage Stability Test on Formulations with PENTA/BMAP

Formulation HL1-72-4 consisted of 3.3 wt % BMAP, 20 wt % AHPMA, 3.8 wt % HEMA, 3.8 wt % TEGDMA, 10.8 wt % UDMA, 1.7 wt % TMPTMA, 4.2 wt % PENTA, 1.7 wt % L-TPO, 0.27 wt % CQ, 0.33 wt % BHT, 33.3 wt % acetone and 16.7 wt % water.

Formulation HL1-72-5 consisted of 6.7 wt % BMAP, 16.7 wt % AHPMA, 3.8 wt % HEMA, 3.8 wt % TEGDMA, 10.8 wt % UDMA, 1.7 wt % TMPTMA, 4.2 wt % PENTA, 1.7 wt % L-TPO, 0.27 wt % CQ, 0.33 wt % BHT, 33.3 wt % acetone and 16.7 wt % water.

The accelerated storage stability test on two PENTA/BMAP based formulations was conducted. The samples HL1-72-4 and HL1-72-5 in black plastic bottles were placed in a 50° C. oven for three weeks. The appearance and pH were checked after one, two and three weeks. The solutions remain clear, colorless and homogeneous. pH did not seem to change. Both samples had good cure under irradiation of Spectrum 800 at 550 mw/cm$^2$ for 20". After one week, the dentin bond strength of HL1-72-4 was reduced to 9.7 (2.9) MPa; after two weeks it was 5.6 (3.5) MPa. After three weeks, the dentin 1P-SEA Example 5

TABLE 3

SEA formulation HL1-126-1 (PENTA/GDMAM as acidic monomers, acetone/water as solvent)

| Formulation Component | | HL1-126-1 % wt |
|---|---|---|
| Glycerol dimethacrylate/maleate (GDMAM) | | 3.3 |
| AHPMA | | 13.3 |
| HEMA | | 10.5 |
| TEGDMA | | 3.9 |
| UDMA | | 11.3 |
| TMPTMA | | 1.7 |
| PENTA | | 4.2 |
| L-TPO | | 1.7 |
| BHT | | 0.13 |
| Acetone | | 33.3 |
| Water | | 16.7 |
| SUM | | 100 |
| Dentin SBS (MPa) | 0 week, 50° C. | 19.4 (3.1) |
| | 2 week, 50° C. | 13.1 (4.2) |
| Enamel SBS (MPa) | 0 week, 50° C. | 24.9 (13.4) |
| | 2 week, 50° C. | 16.8 (5.4) |

1P-SEA Example 6

TABLE 4

Formulations with EGMP as acidic monomer and water/ethanol as solvent

| Formulation Component | HL1-25 % wt | HL1-27 % wt | HL1-28 % wt | HL1-30 % wt | HL1-33 % wt | HL1-39 % wt |
|---|---|---|---|---|---|---|
| EGMP | 20 | 20 | 20 | 20 | 20 | 12 |
| BMAP | 0 | 0 | 0 | 0 | 0 | 8 |
| HEMA | 10 | 14.6 | 12.6 | 16.6 | 10 | 12.6 |
| AHPMA | 0 | 0 | 0 | 0 | 7.6 | 0 |
| TEGDMA | 10 | 10 | 10 | 10 | 10 | 10 |
| UDMA | 5 | 5 | 10 | 10 | 5 | 5 |

TABLE 4-continued

Formulations with EGMP as acidic monomer and water/ethanol as solvent

| Formulation Component | HL1-25 % wt | HL1-27 % wt | HL1-28 % wt | HL1-30 % wt | HL1-33 % wt | HL1-39 % wt |
|---|---|---|---|---|---|---|
| TMPTMA | 2 | 2 | 2 | 2 | 2 | 2 |
| PENTA | 0 | 5 | 0 | 0 | 0 | 5 |
| L-TPO | 2 | 2 | 4 | 0 | 4 | 5 |
| CQ | 0.2 | 0.2 | 0.2 | 0.2 | 0.2 | 0 |
| EDAB | 0.8 | 0.8 | 0.8 | 0.8 | 0.8 | 0 |
| BHT | 0.4 | 0.4 | 0.4 | 0.4 | 0.4 | 0.4 |
| Ethanol | 20 | 20 | 20 | 20 | 20 | 20 |
| Water | 30 | 20 | 20 | 20 | 20 | 20 |
| SUM | 100 | 100 | 100 | 100 | 100 | 100 |
| Dentin SBS (MPa) | 4.9(2.1) | 4.2(1.1) | 6.3(1.4) | No cure | 5.0(1.0) | 5.0(1.6) |

TABLE 5

Formulations with EGMP as acidic monomer and water/acetone as solvent

| Formulation Component | HL1-38 % wt | HL1-47 % wt |
|---|---|---|
| EGMP | 20 | 25 |
| HEMA | 12.6 | 15.8 |
| TEGDMA | 10 | 15.9 |
| UDMA | 5 | 6.3 |
| TMPTMA | 2 | 2.5 |
| PENTA | 5 | 6.3 |
| L-TPO | 5 | 2.5 |
| CQ | 0 | 0.4 |
| BHT | 0.4 | 0.5 |
| Acetone | 20 | 25 |
| Water | 20 | 0 |
| SUM | 100 | 100 |
| Dentin SBS (MPa) | 5.6 (1.7) | 4.9 (0.8) |

1P-SEA Example 7

0.3% cetylamine hydrofluoride (CAF) and 2% Aerosil R974 were added to HL1-203 and HL2-40 for filled and fluoride-releasing one-part SEA. The dentin and enamel SBS of the baseline and 50° C. aged samples are summarized in Table 6. Like the base formulations, 3-week 50° C. aged HL2-87-1 and HL2-87-2 both still had good bond strength on dentin and enamel. It is noteworthy that 4-week 50° C. aged HL2-87-1 and HL2-87-2 had dentin SBS 18.7 MPa and enamel SBS 16.7 MPa, respectively, significantly higher than their corresponding base formulations. Their enamel bond strength, however, was not so different from their base formulations.

TABLE 6

Bond strength and storage stability of one-part SEA filled with CAF and Aerosil R974

| | | Sample I.D. | |
|---|---|---|---|
| | | HL2-87-1 HL2-40 + 0.3% CAF + 2% Aerosil 974 | HL2-87-2 HL1-203 + 0.3% CAF + 2% Aerosil 974 |
| Sample composition | | | |
| Human Dentin SBS (MPa): Mean (SD) | RT stored | 19.8 (5.5) | 13.6 (5.7) |
| | 3 week 50° C. | 22.0 (3.5) | 21.8 (4.7) |
| | 4 week 50° C. | 18.7 (5.1) | 16.7 (9.4) |

TABLE 6-continued

Bond strength and storage stability of one-part SEA filled with CAF and Aerosil R974

| | | Sample I.D. | |
|---|---|---|---|
| | | HL2-87-1 HL2-40 + 0.3% CAF + 2% Aerosil 974 | HL2-87-2 HL1-203 + 0.3% CAF + 2% Aerosil 974 |
| Sample composition | | | |
| | RT stored | 29.2 (5.1) | 27.8 (15.4) |
| | 3 week 50° C. | 21.0 (6.3) | 21.0 (11.2) |
| | 4 week 50° C. | 10.2 (6.4) | 9.4 (3.2) |

1P-SEA Example 8

0.3% CAF and 2% Dentsply proprietary nanofiller were added to HL1-203 and HL2-40 for filled and fluoride-releasing one-part SEA. Bond strength and 50° C. storage stability are summarized in Table 7. It seems that HL1-230 is not very compatible with Nanofiller. Somehow, HL2-107-1, the filled version of HL1-203 did not show good enamel bond strength. HL2-107-2, the filled version of HL2-40, had good dentin and enamel bond strength for the samples stored at 50° C. up to three weeks, 16.6 MPa on dentin and 24.7 MPa on enamel. More interestingly, after storage at 50° C. for 4 weeks, its dentin and enamel SBS are 16.8 MPa and 18.3 MPa, respectively, significantly higher than its non-filled counterpart.

TABLE 7

Bond strength of one-part SEA filled with CAF and nanofiller

| | | Sample I.D. | |
|---|---|---|---|
| | | HL2-107- HL1-203 + 0.3% CAF + 2% Nanofiller | HL2-107-2 HL2-40 + 0.3% CAF + 2% Nanofilller |
| Sample composition | | | |
| Human Dentin SBS (MPa): Mean (SD) | RT stored | 17.2 (4.4) | 24.5 (4.5) |
| | 3 week 50° C. | 17.3 (7.9) | 16.6 (4.5) |
| | 4 week 50° C. | | 16.8 (8.5) |
| Human Enamel SBS (MPa): Mean (SD) | RT stored | 14.1 (0.4) | 35.7 (6.0) |
| | 3 week 50° C. | 16.6 (8.3) | 24.7 (4.7) |
| | 4 week 50° C. | | 18.3 (5.6) |

1P-SEA Example 9

A mixture comprising 20.0 parts by weight of dipentaerythritol pentaacrylate phosphoric acid ester (PENTA), 6.9 parts by weight of 3-(acryloyloxy)-2-hydroxypropyl methacrylate (AHPMA), 5.0 parts by weight of 2-hydroxyethyl methacrylate (HEMA), 8.0 parts by weight of 1,6-Bis (methacryloyloxyethoxycarbonylamino)-2,4,4-trimethylhexane (UDMA), 2.0 parts by weight of trimethylolpropane trimethacrylate (TMPTMA), 1.7 parts by weight of diphenyl (2,4,6-trimethylbenzoyl) phosphine oxide, 0.30 parts by weight of camphouquinone (CQ), and 1.0 parts of 4-dimethylaminobenzonitrile (DMABN) or 1.0 parts of EDAB, 0.2 part by weight of butylated hydroxytoluene, 0.2 parts of cetylamine hydrofluoride (CAF), 41.0 parts by weight of acetone and 13.7 parts by weight of deionized water were prepared. The composite to dentin and enamel bond strength was measured as 22.5 MPa and 25.3 MPa, respectively. When the 1P-SEA was used with Self Cure Activator component, the 24 hour composite resin cement (Calibra) to dentin and enamel bond strength was measured as 16.0 MPa and 22.0 MPa, respectively, without separate etching step.

1P-SEA Example 10

As described in the previous patent examples, 1P-SEA formulations can use initiators combination of L-TPO and CQ with different coinitiators (different amines, such as DMABN, EDAB, or DHEPT) to make the 1P-SEA compatible with both dental halogen QTH or LED curing lights. Table 8 compares bond strength of three different experimental 1P-SEA differing only in aromatic amines. DHEPT and EDAB are two most commonly used co-initiators for CQ. The formulations containing either DHEPT or EDAB did not lead to acceptable balanced properties. Only the formulation incorporating DMABN exhibits the superior balance of bond strength, storage stability and compatibility with different curing lights (dental QTH and LED curing lights). DMABN is the first time ever used in any commercial dental adhesive.

TABLE 8

24 hr Shear Bond Strength of 1P-SEA Containing Different Co-initiators

| Sample I.D. | | | 1P-SEA containing DMABN | 1P-SEA containing DHEPT | 1P-SEA containing EDAB |
|---|---|---|---|---|---|
| Human Dentin SBS (MPa): Mean (SD) | RT | QTH Light | 23.2 (3.9) | NT | 17.0 (7.5) |
| | stored | LED light | 22.0 (4.0) | NT | 15.6 (5.7) |
| | 50° C. 3 | QTH Light | 15.3 (4.2) | NT | 14.5 (6.9) |
| | weeks | LED light | 15.8 (6.1) | NT | 16.8 (6.8) |
| Human Enamel SBS (MPa): Mean (SD) | RT | QTH Light | 26.4 (5.3) | 13.5 (6.7) | 32.7 (7.2) |
| | stored | LED light | 32.0 (3.0) | NT | 30.1 (7.3) |
| | 50° C. 3 | QTH Light | 26.7 (5.3) | NT | 7.6 (2.0) |
| | weeks | LED light | 35.3 (7.9) | NT | 24.8 (13.3) |

What is claimed is:

1. A dental adhesive comprising:
(i) from about 5 to about 70% by weight of polymerizable acids components selected from the group consisting of dipentaerythritol pentaacrylate phosphoric acid ester, 4,4'-oxydiphenylether 1,1',6,6'-tetracarboxylic acid-1,1'-(2-metharcyloxy)dimethacrylate and mixtures thereof;
(ii) from about 1 to about 30% by weight of hydrophilic methacrylate;
(iii) from about 1 to about 25% by weight of hydrophilic difunctional (meth)acrylate;
(iv) from about 1 to about 30% by weight of hydrophobic difunctional (meth)acrylate;
(v) from about 0.1 to about 5% by weight photoinitiators selected from the group consisting of diphenyl (2,4,6-trimethylbenzoyl)phosphine oxide, camphorquinone/dimethylaminobenzonitrile combination and diphenyl (2,4,6-trimethylbenzoyl)phosphine oxide/camphorquinone/4-ethyldimethylaminbenzoate combination;
(vi) from about 0.1 to about 5% by weight curing additives selected from the group consisting of aromatic sulfinate salts;
(vii) from about 0.1 to about 5% by weight cetylamine hydrofluoride;
(viii) from about 0.05 to about 2% stabilizer;
(ix) from about 1 to about 40% water; and
(x) from about 5 to about 60% water-miscible polar organic solvent selected from the group consisting of acetone and alcohol.

2. A dental adhesive comprising:
(i) from about 5 to about 50% by weight of polymerizable acids components selected from the group consisting of dipentaerythritol pentaacrylate phosphoric acid ester, 4-methacryloxyethyltrimellitic anhydride and mixtures thereof;
(ii) from about 1 to about 20% by weight of hydrophilic methacrylate;
(iii) from about 1 to about 15% by weight of hydrophilic difunctional (meth)acrylate;
(iv) from about 1 to about 30% by weight of hydrophobic difunctional (meth)acrylate;
(v) from about 0.1 to about 5% by weight photoinitiators selected from the group consisting of diphenyl (2,4,6-trimethylbenzoyl)phosphine oxide, camphorquinone/dimethylaminobenzonitrile combination and diphenyl (2,4,6-trimethylbenzoyl)phosphine oxide/camphorquinone/4-ethyldimethylaminbenzoate combination;
(vi) from about 0.1 to about 5% by weight cetylamine hydrofluoride;
(vii) from about 0.05 to about 2% by weight stabilizer;
(viii) from about 1 to about 35% by weight water; and
(ix) from about 5 to about 60% by weight water-miscible polar organic solvent selected from the group consisting of acetone or alcohol.

3. The dental adhesive of claim 2, wherein the hydrophilic difunctional (meth)acrylate comprises 3-(acryloyloxy)2-hydroxypropyl methacrylate.

4. The dental adhesive of claim 2, wherein the hydrophobic difunctional (meth)acrylate is a urethane dimethacrylate.

5. The dental adhesive of claim 4, wherein the urethane dimethacrylate is 1,6-bis[methacryloyloxyethoxycarbonylamino]-2,4,4-trimethylhexane.

6. The dental adhesive of claim 2, wherein the hydrophilic methacrylate comprises 2-hydroxyethyl methacrylate.

* * * * *